(12) United States Patent
Liang et al.

(10) Patent No.: US 12,285,577 B2
(45) Date of Patent: Apr. 29, 2025

(54) ATRIAL SHUNT DEVICE, MANUFACTURING METHOD, AND ATRIAL SHUNT SYSTEM USING SHUNT DEVICE

(71) Applicant: Chenxing (Nantong) Medical Equipment Co., Ltd., Nantong (CN)

(72) Inventors: Yuchen Liang, Nantong (CN); Chengwen Jiang, Nantong (CN); Zhongliang Xiong, Nantong (CN); Meihui Zhang, Nantong (CN)

(73) Assignee: CHENXING (NANTONG) MEDICAL EQUIPMENT CO., LTD., Nantong (CN)

( * ) Notice: Subject to any disclaimer, the term of this patent is extended or adjusted under 35 U.S.C. 154(b) by 0 days.

(21) Appl. No.: 18/705,844

(22) PCT Filed: Sep. 2, 2022

(86) PCT No.: PCT/CN2022/116802
§ 371 (c)(1),
(2) Date: Apr. 29, 2024

(87) PCT Pub. No.: WO2023/030494
PCT Pub. Date: Mar. 9, 2023

(65) Prior Publication Data
US 2024/0325698 A1    Oct. 3, 2024

(30) Foreign Application Priority Data

Sep. 2, 2021   (CN) .......................... 202111029141.2
Sep. 28, 2021  (CN) .......................... 202111141927.3

(51) Int. Cl.
*A61M 27/00*   (2006.01)

(52) U.S. Cl.
CPC ... *A61M 27/002* (2013.01); *A61M 2205/0216* (2013.01); *A61M 2205/025* (2013.01);
(Continued)

(58) Field of Classification Search
CPC ........ A61M 27/002; A61M 2205/0216; A61M 2205/025; A61M 2205/0266; A61M 2207/10; A61M 2209/04; A61M 2210/125
See application file for complete search history.

(56) References Cited

U.S. PATENT DOCUMENTS

| | | | | |
|---|---|---|---|---|
| 2002/0198561 | A1* | 12/2002 | Amplatz | .......... A61B 17/12109 |
| | | | | 606/200 |
| 2009/0082803 | A1* | 3/2009 | Adams | ............. A61B 17/12113 |
| | | | | 606/213 |

(Continued)

FOREIGN PATENT DOCUMENTS

| | | |
|---|---|---|
| CN | 103284767 A | 9/2013 |
| CN | 106714698 A | 5/2017 |

(Continued)

*Primary Examiner* — Susan S Su
*Assistant Examiner* — Erin A Kim
(74) *Attorney, Agent, or Firm* — MUNCY, GEISSLER, OLDS & LOWE, P.C.

(57) ABSTRACT

This invention pertains to the field of medical devices and specifically relates to an atrial shunt device and its manufacturing method, as well as the application of this device in an atrial shunt system. The atrial shunt comprises a middle channel structure with left atrial wall fixing structures and right atrial wall fixing structures on both sides. The left atrial wall fixing structure is a woven network structure formed by weaving threads through a weaving process, and it includes at least two layers of woven layers. By employing a multi-layer woven structure, this invention enhances the waist support compared to traditional single-layer woven structures, reduces the risk of opening blockage caused by excessive intimalization, lowers atrial pressure, improves patient cardiac function, and prolongs patient life.

17 Claims, 15 Drawing Sheets

(52) U.S. Cl.
CPC . *A61M 2205/0266* (2013.01); *A61M 2207/10* (2013.01); *A61M 2209/04* (2013.01); *A61M 2210/125* (2013.01)

(56) References Cited

U.S. PATENT DOCUMENTS

| | | | |
|---|---|---|---|
| 2009/0099647 A1* | 4/2009 | Glimsdale | A61B 17/12172 623/1.35 |
| 2013/0190676 A1* | 7/2013 | Dickinson | A61F 2/07 604/8 |
| 2017/0113026 A1* | 4/2017 | Finch | A61B 17/11 |
| 2017/0273790 A1* | 9/2017 | Vettukattil | A61F 2/2493 |
| 2017/0333060 A1* | 11/2017 | Panian | A61M 25/005 |
| 2020/0254228 A1* | 8/2020 | Taft | A61F 2/06 |
| 2020/0390944 A1* | 12/2020 | Williams | A61F 2/30721 |
| 2021/0085935 A1* | 3/2021 | Fahey | A61B 17/11 |
| 2022/0241565 A1* | 8/2022 | Nae | A61B 17/11 |

FOREIGN PATENT DOCUMENTS

| | | |
|---|---|---|
| CN | 210962104 U | 7/2020 |
| CN | 112402062 A | 2/2021 |
| CN | 112674809 A | 4/2021 |
| CN | 113729800 A | 12/2021 |

\* cited by examiner

ATRIAL SHUNT DEVICE, MANUFACTURING METHOD, AND ATRIAL SHUNT SYSTEM USING SHUNT DEVICE

CROSS-REFERENCE TO RELATED APPLICATIONS

The present application is a U.S. national phase of International Application No. PCT/CN2022/116802, filed Sep. 2, 2022; and this application claims priority of application No. 202111029141.2, filed in China on Sep. 2, 2021, and application No. 202111141927.3, filed in China on Sep. 28, 2021, the entire contents of all of which are hereby incorporated by reference.

TECHNICAL FIELD

The present invention relates to the field of medical devices, specifically involving an atrial shunt device, its manufacturing method, and a shunt system using the shunt device.

BACKGROUND

Heart failure (HF), abbreviated as heart failure, is the final common manifestation of myocardial disease caused by various reasons. According to current guidelines, heart failure can be divided into three types: heart failure with reduced ejection fraction (HFrEF), heart failure with mid-range ejection fraction (HFmrEF), and heart failure with preserved ejection fraction (HFpEF).

HFpEF refers to heart failure with an ejection fraction greater than 50%, primarily characterized by a decrease in cardiac diastolic function and compliance rather than a decrease in systolic function. Clinical epidemiological data show that in hospitalized heart failure populations, more than half of the patients have HFpEF or HFmrEF. HFpEF and HFrEF exhibit similar long-term mortality and complication rates. The data indicate a significant increase in the incidence of HFpEF over the past 15 years, possibly associated with population aging. HFpEF is mainly observed in elderly patients, postmenopausal women, individuals with obesity, hypertension, diabetes, and microangiopathic myocardial ischemia, etc., are risk factors for HFpEF. With the increasing trend of population aging in today's society, the incidence of HFpEF is expected to continue to rise year by year.

The main pathophysiologic processes of HFpEF include impaired left ventricular diastolic filling function and elevated left ventricular end-diastolic pressure due to systemic inflammation, inflammation and accumulation of epicardial adipose tissue, secretion of adipose inflammatory factors, coronary microcirculatory vascular dysfunction, myocardial fibrosis, and increased ventricular and arterial stiffness, which further lead to left atrial dysfunction, elevated left atrial filling pressures, and electrical activity disturbances. Clinical manifestations of HFpEF include elevated left ventricular end-diastolic pressure (LVEDP) and pulmonary capillary wedge pressure (PCWP)/left atrial pressure (LAP) at rest and under load, ultimately leading to pulmonary edema and postcapillary pulmonary arterial hypertension.

Currently, there are no effective treatments for HFpEF. Research shows that traditional treatments such as angiotensin pathway inhibitors, beta-blockers, aldosterone receptor antagonists, calcium channel blockers, etc., although partially reversing left ventricular hypertrophy, relaxing myocardium, and improving diastolic function, do not improve patient prognosis and reduce cardiovascular mortality. So far, the treatment of HFpEF, apart from using diuretics to control reduced volume load, controlling hypertension and diabetes, and controlling atrial fibrillation rhythm, is almost non-existent.

The two main techniques available that are still in the clinical stage are atrial shunts made of nickel-titanium alloy and atrial shunts using a single woven layer. Both methods have been clinically proven to be effective. However, the nickel-titanium alloy structure has overall high strength, requiring the use of large-diameter delivery devices, which can cause significant harm to patients. The single-layer woven atrial shunt device, despite being usable with small-diameter delivery devices, lacks radial support and is prone to reocclusion at the opening site due to excessive intimalization. Therefore, it is necessary to improve these devices to overcome the shortcomings in practical applications.

SUMMARY

The present invention aims to provide an atrial shunt, a manufacturing method thereof and a shunt system to address technical issues in existing atrial shunt devices, specifically the excessive strength requiring the use of large-diameter delivery devices and the insufficient support leading to recurrent blockages.

An atrial shunt device comprising a middle channel structure with left atrial wall fixing structure and right atrial wall fixing structure on either side;
wherein the left atrial wall fixing structure is a woven mesh structure woven from one or more wires using a braiding process, and the woven mesh structure includes at least two layers of woven layers.

In one embodiment, the atrial shunt device includes an woven long cylinder and a delivery device connection structure for connection to a delivery device. The woven long cylinder structure is folded inward or outward from the middle waist to form overlapping inner and outer woven layers, with the inner woven layer forming a connecting channel.

The proximal ends of the inner and outer woven layers overlap and are bound radially to form a tail section. The proximal end of the device is formed with a communication port in communication with the connecting channel, and the delivery device connection structure tightens the tail section. The inner and outer woven layers are heat-set to form the right atrial wall fixing structure, the middle channel structure, and the left atrial wall fixing structure sequentially along the axis direction of the atrial shunt device.

In one embodiment, the device has 8 to 20 grids per inch.

The distal ends of the inner woven layer and the outer woven layer are overlapped and fixed by a fixing member, bringing the distal ends of the inner woven layer and the outer woven layer into close contact.

In one embodiment, the distal ends of the inner woven layer and the outer woven layer are overlapped and braided together with one or more wires.

The left atrial wall fixing structure is inclined towards the middle channel structure, and the cross-sectional angle between the left atrial wall fixing structure and the middle channel structure is an acute angle.

The angle of the acute angle is 40° to 80°.

The left atrial wall fixing structure is woven from at least two wires.

The one or more wires are selected from nickel-titanium wire, platinum-iridium wire, or a combination thereof.

The diameter of the wire is 0.08 mm to 0.15 mm.

The woven mesh structure comprises 2 to 4 layers of woven layers, preferably the woven mesh structure is a double-layer woven mesh structure comprising two woven layers.

The middle channel structure and the right atrial wall fixing structure use the same wires and the same number of woven layers as the left atrial wall fixing structure. The left atrial wall fixing structure, middle channel structure, and right atrial wall fixing structure are integrally woven and then thermally set.

In one embodiment, the atrial shunt device further includes a delivery device connection structure, which is connected to the right atrial wall fixing structure at the distal end and can be connected to the delivery device at the proximal end. The delivery device connection structure is a hollow cylindrical structure, and its distal end is used to retract and secure the wires by means of a press fit. The outer peripheral surface of the delivery device connection structure has a ring of grooves, which hold an external ring sleeve for the retrieval of the atrial shunt device.

The proximal end of the delivery device connection structure has internal or external threads for connection to the delivery device via threaded connection.

The material of the delivery device connection structure is selected from stainless steel, nickel-titanium alloy, platinum-iridium alloy, or a combination thereof.

The atrial shunt device further includes a connecting channel running through the middle of the left atrial wall fixing structure, middle channel structure, and right atrial wall fixing structure.

The diameters of the left atrial wall fixing structure and the right atrial wall fixing structure are both 15 mm to 25 mm.

The middle channel structure is a hollow cylindrical structure with openings on the left and right sides. The central portion of the hollow cylindrical structure serves as the connecting channel. The proximal outer peripheral end of the middle channel structure is connected to the right atrial wall fixing structure, and the distal outer peripheral end is connected to the left atrial wall fixing structure.

The inner diameter of the hollow cylindrical structure is 3 mm to 15 mm, and the length is 5 mm to 15 mm.

The positive progress of the present invention is that it uses an atrial shunt device with a woven structure, which, compared to traditional alloy structures, can be delivered using a smaller-diameter delivery device, reducing patient harm and improving surgical success rates and operational convenience. The atrial shunt device employs a multi-layer woven structure, which, compared to traditional single-layer woven structures, enhances lumbar support, reduces reocclusion due to excessive intimalization, lowers atrial pressure, improves patient cardiac pressure, and extends patient lifespan.

The present invention also provides a method for manufacturing the atrial shunt device, including the following steps:

integrally weaving to form an woven long cylinder;

folding the woven long cylinder outward or inward from the middle waist to form overlapping inner woven layers and outer woven layers, with the inner woven layer forming a connecting channel;

after the proximal ends of the inner woven layer and the outer woven layer overlap, they are bent radially and bound together to form a tail section, and a communication port is formed at the proximal end of the atrial shunt device, communicating with the connecting channel;

tightening the tail section to form a workpiece awaiting heat setting;

heat-setting the workpiece awaiting heat setting to form the right atrial wall fixing structure, middle channel structure, and left atrial wall fixing structure sequentially arranged from proximal to distal, with the tail section located on the right atrial wall fixing structure;

fixing the tail section with a delivery device connection structure for connection to a delivery device.

Since the left atrial wall fixing structure, middle channel structure, and right atrial wall fixing structure are made by integrally weaving an woven long cylinder, the weaving density at various locations on the cylinder can be identical. Therefore, in the actual production process, a machine can be used to weave the cylinder, greatly reducing the weaving difficulty.

Moreover, by directly folding the woven long cylinder, it is possible to obtain inner and outer woven layers without the need for layer-by-layer weaving (in the existing process of weaving the middle channel structure, two layers are generally woven first, and then the two layers are sewn together). This significantly reduces the producing difficulty of the atrial shunt device. Simultaneously, by cleverly overlapping and then bending and tying the proximal ends of the inner and outer woven layers in a radial direction, a communication port in communication with the connecting channel is formed at the proximal end of the atrial shunt device. Additionally, a tail section that can be fixed with a delivery device fixation structure is retained, achieving a two-in-one solution. With the ingenious manufacturing method in this application, an ideal double-layer woven atrial shunt device can be obtained with the simplest processing.

Furthermore, by folding the woven long cylinder, which forms the inner and outer woven layers, the atrial shunt device not only obtains sufficient elasticity but also, due to having two layers of woven mesh, has enough wires in contact with the atrial wall to ensure sufficient intimalization.

By using the double-layer woven form with the inner and outer woven layers, the woven density of both layers does not need to be too high, facilitating subsequent heat setting of the atrial shunt device. If the weaving is too dense, the woven layers become stiff, making heat setting impossible or quite hard.

In summary, the atrial shunt device in this application, using the form of the inner and outer woven layers, can be machine-woven and still retains high resilience, and can achieve optimal intimalization with the atrial wall.

In one embodiment, before heat setting the workpiece awaiting heat setting, one or more wires are used to reinforce the distal ends of the inner and outer woven layers, ensuring a snug fit between the distal ends of the inner and outer woven layers.

In one embodiment, the heat setting step of the workpiece awaiting heat setting specifically includes the following steps:

locating a shaping rod in the communication port and the connecting channel;

shaping the workpiece awaiting heat setting into the shapes of the right atrial wall fixing structure, middle channel structure, and left atrial wall fixing structure with mold components to form a to-heat piece;

placing the to-heat piece into a heating furnace for heat treatment;
cooling the completed heated atrial shunt device.

The present invention also provides a shunt system for the atria, including the atrial shunt device mentioned above and an atrial shunt device delivery device.

The atrial shunt device delivery device has a catheter sheath structure, which includes:
a pre-bent sheath tube with a bent shape at a distal end; and
a catheter sheath handle, connected to a proximal end of the pre-bent sheath tube, the catheter sheath handle having a hollow cylindrical main body, and the interior of the main body having a sealing pad with a needle hole, wherein the sealing pad has a sealing flat pad and a sealing bent pad, the sealing bent pad tightly abuts against the sealing flat pad.

In one embodiment, the curvature radius of the sealing bent pad is 10 mm to 15 mm, preferably 12 mm to 13 mm. The raised side of the sealing bent pad is at the distal end, and the concave side is at the proximal end.

The catheter sheath handle has a hollow sheath connection portion, a hollow middle portion, and a hollow loading connection portion successively from the distal end to the proximal end. The sealing bent pad and the flat seal pad tightly fit at the proximal end of the middle portion.

The present invention adjusts the curved sealing pad in the handle of the existing catheter sheath to a double-layer sealing pad. The thickness of each layer of the sealing pad is only half of that of the sealing pad in the existing technology. Additionally, the sealing pad near the proximal end is changed to a flat shape, while the sealing pad at the distal end remains curved. However, the curvature radius of the sealing pad is much larger than that of the sealing pad in the existing technology. If the curvature of the sealing pad is too high, it may easily lead to insufficient sealing when the instrument passes through. Therefore, this invention adjusts the curvature radius, thus ensuring both easy passage of the instrument and sealing performance. The flat sealing pad ensures sealing when no instrument is passing through. Furthermore, the entire edge of the sealing pad is consistent with the middle thickness, preventing the occurrence of fractures and improving the lifespan.

The inventive design of the atrial shunt device delivery device achieves an economically practical structure tailored to reduce patient harm, improve surgical success rates, and facilitate surgery. Simultaneously, it reduces costs, benefiting a large number of patients and their families.

REFERENCE NUMERALS

Figure 1:
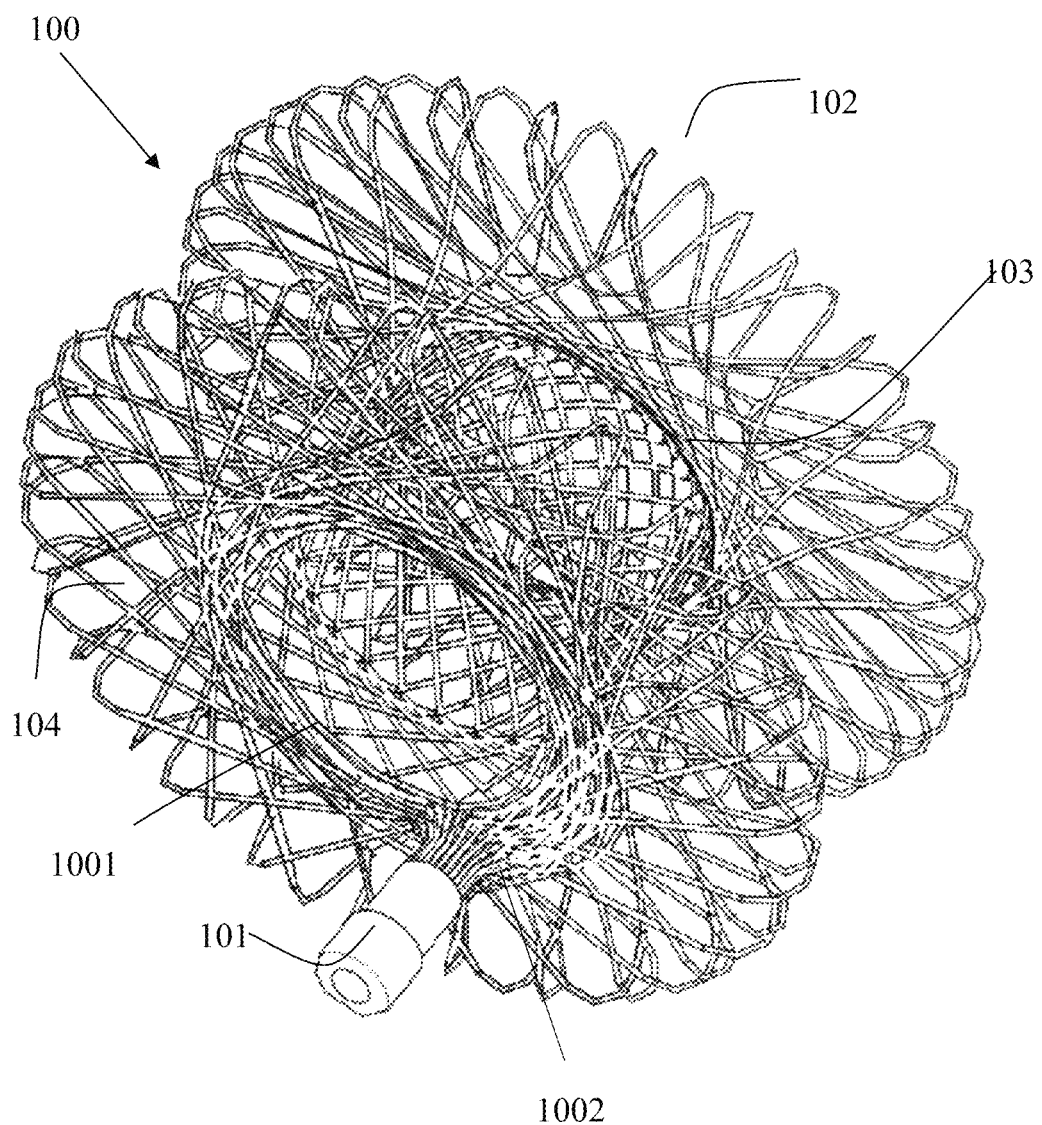
FIG. 1 depicts a three-dimensional view of the first embodiment of the present invention.

100: Atrial shunt device
101: Delivery device connection structure
102: Left atrial wall fixing structure
103: Middle channel structure
104: Right atrial wall fixing structure
105: Connecting channel
106: Groove
107: Woven long cylinder
108: Inner woven layer
109: Outer woven layer
1001: Communication port
1002: Tail section
1003: Proximal end of the atrial shunt device 300: Atrial wall
401: Shaping rod
402: Middle mold
403: Left mold
404: Right mold

DETAILED DESCRIPTION OF THE EMBODIMENTS

In order to facilitate a clear understanding of the technical means, creative features, and the achievement of objectives and effects of the present invention, the following detailed description is provided in conjunction with specific drawings.

Embodiment 1

Referring to FIGS. 1 to 4, the first embodiment of the present invention provides an atrial shunt device 100. The atrial shunt device 100 includes a left atrial wall fixing structure 102, a middle channel structure 103, and a right atrial wall fixing structure 104. The left atrial wall fixing structure 102 and the right atrial wall fixing structure 104 are respectively arranged on both sides of the middle channel structure 103. A connecting channel 105 passes through the center of the left atrial wall fixing structure 102, the middle channel structure 103, and the right atrial wall fixing structure 104.

The left atrial wall fixing structure 102 is a woven mesh structure woven from wires using braiding techniques. The woven mesh structure includes at least two layers of woven layers.

Specifically, the left atrial wall fixing structure 102 is woven from at least two wires. The specific number of wires can be adjusted according to actual needs, as long as it does not depart from the scope of the present invention. The wires are nickel-titanium wires, platinum-iridium wires, or a combination thereof. Preferably, the diameter of the wires is 0.08 mm to 0.15 mm. Due to the small diameter of the wires, the atrial shunt device 100 can have a reduced impact on the human body. The woven mesh structure is composed of 2 to 4 layers of woven layers, meaning that one layer of woven mesh is woven from wires through braiding techniques, and multiple layers of woven layers constitute the final woven mesh structure. Preferably, the woven mesh structure is a double-layer woven mesh structure composed of two layers of woven layers. The double-layer woven mesh structure, while saving materials, provides better elasticity and fatigue resistance, and sufficient support to prevent occlusion caused by excessive endothelialization.

The diameters of the left atrial wall fixing structure 102 and the right atrial wall fixing structure 104 are both 15 mm to 25 mm.

Furthermore, preferably, the middle channel structure 103 and the right atrial wall fixing structure 104 use the same wires and the same number of layers of woven layers as the left atrial wall fixing structure 102. For example, it can be two layers, three layers, four layers, etc., and the number of woven layers can be adjusted as needed. Preferably, the left atrial wall fixing structure 102, the middle channel structure 103, and the right atrial wall fixing structure 104 are integrally woven and then thermally shaped. Since they are integrally woven, the atrial shunt device 100 can be woven in one step using mechanical weaving, reducing manual involvement. The above process of the present invention can provide sufficient structural stability while being easy to manufacture.

The middle channel structure 103 is a hollow cylindrical structure with open ends on both the left and right sides. The central portion of the hollow cylindrical structure serves as the connecting channel 105. The outer circumferential surface end of the near end of the middle channel structure 103 is connected to the right atrial wall fixing structure 104, and the outer circumferential surface end of the far end is connected to the left atrial wall fixing structure 102. Preferably, the inner diameter of the hollow cylindrical structure is 3 mm to 15 mm, and the length is 5 mm to 15 mm.

Figure 2:
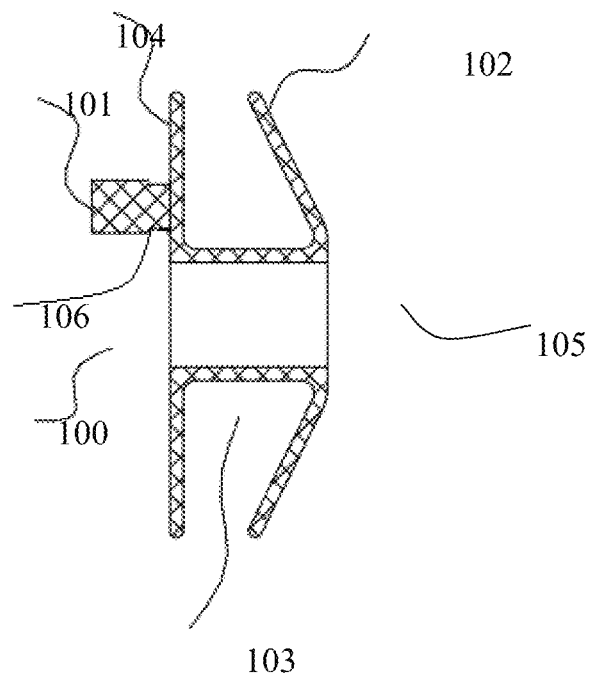
FIG. 2 illustrates a cross-sectional schematic view of the first embodiment of the present invention.
Figure 3:
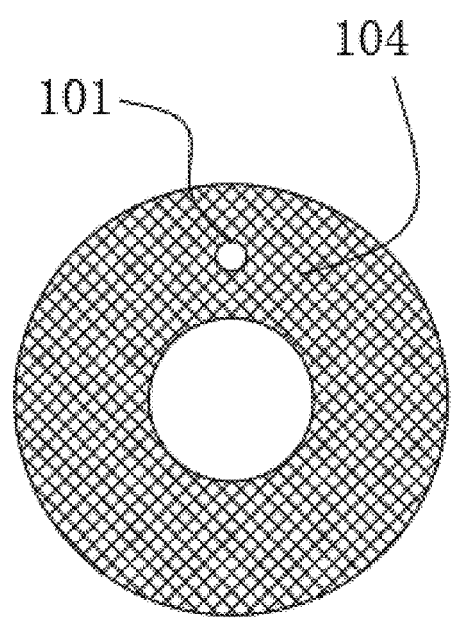
FIG. 3 is a front schematic view of the first embodiment of the present invention.
Figure 4:
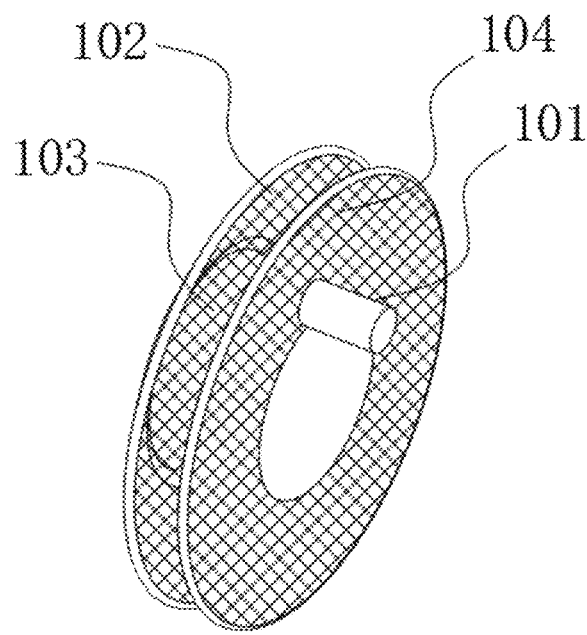
FIG. 4 is an axonometric schematic view of the first embodiment of the present invention.

Referring to FIG. 2, the left atrial wall fixing structure 102 is inclined towards the middle channel structure 103 and forms an acute angle with the cross-section of the middle channel structure 103. The angle between the cross-section of the left atrial wall fixing structure 102 and the middle channel structure 103 is an acute angle, with an angle of 40° to 80°. The left atrial wall fixing structure 102, in this configuration, forms a reverse "C" shape. The use of a reverse "C" shaped structure allows for a tighter connection between the left atrial wall fixing structure 102 and the left atrial wall. Additionally, for different patients, the thickness of the atrial wall 300 may vary. When the left atrial wall fixing structure 102 forms a reverse "C" shaped structure, it allows for elastic deformation of the left atrial wall fixing structure 102, enabling the atrial shunt device 100 to adapt to different thicknesses of the atrial wall 300 in different patients, thereby improving the versatility of the atrial shunt device 100.

The atrial shunt device 100 further comprises a delivery device connection structure 101, and the material of the delivery device connection structure 101 is selected from stainless steel, nitinol alloy, platinum-iridium alloy, or combinations thereof. The distal end of the delivery device connection structure 101 is connected to the right atrial wall fixing structure 104, while the proximal end can be connected to a delivery device. The proximal end of the delivery device connection structure 101 is provided with internal threads or external threads, allowing it to be threadedly connected to the delivery device through internal threads or external threads. The delivery device connection structure 101 is a hollow cylindrical structure, and its distal end compressively secures and fixes the wires, achieving a connection with the right atrial wall fixing structure 104. A ring of grooves 106 is provided on the outer circumferential surface of the delivery device connection structure 101, which can be used for the retrieval of the atrial shunt device 100 by engaging with an external loop during retrieval. Preferably, the grooves 106 are positioned on the side closer to the distal end. The delivery device connection structure 101 is designed to fix the braided lines, connect with the delivery device's pusher 201, and provide digital subtraction angiography (DSA) imaging functionality.

During the implementation of the atrial shunt device 100 according to the present invention, with the assistance of an external delivery device, the device is delivered to the opening between the left atrium and right atrium through the "transseptal technique" (i.e., inserting a catheter into the right femoral vein, advancing it upwards through the inferior vena cava into the right atrium, puncturing the septum, and then inserting the catheter into the left atrium). The delivery device establishes a pathway through the right femoral vein, creates an opening in the left and right atrial walls using tools, and finally delivers the atrial shunt device 100 to the opening with the assistance of the delivery device.

Figure 5:
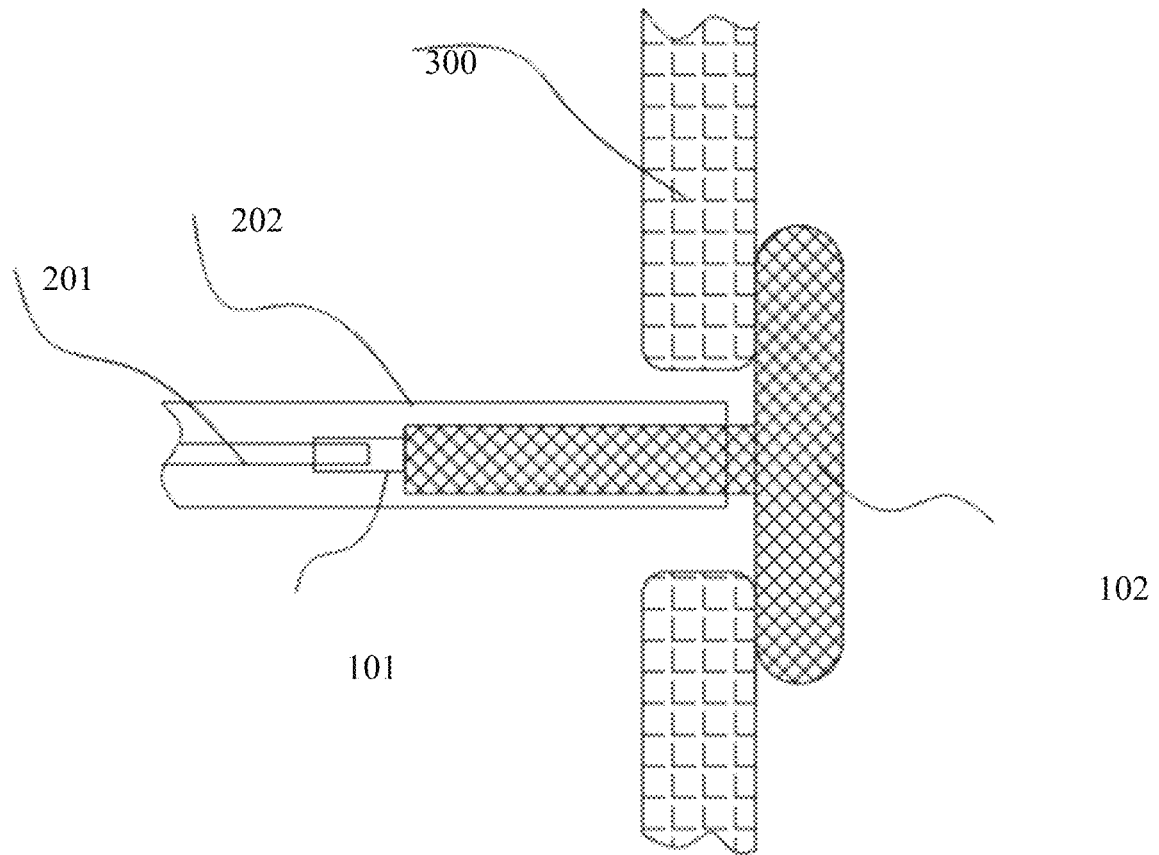
FIG. 5 illustrates a schematic diagram of a release state of the left atrial wall fixing structure during the implementation of the first embodiment of the present invention.

Referring to FIG. 5, the pusher 201 of the delivery device is in communication with the delivery device connection structure 101. In the pathway established by the delivery device's catheter sheath 202, the pusher 201 delivers the atrial shunt device into the left atrium. By manipulating the pusher 201, the left atrial wall fixing structure 102 is released from the catheter sheath 202, allowing it to adhere to the left atrial wall.

Figure 6:
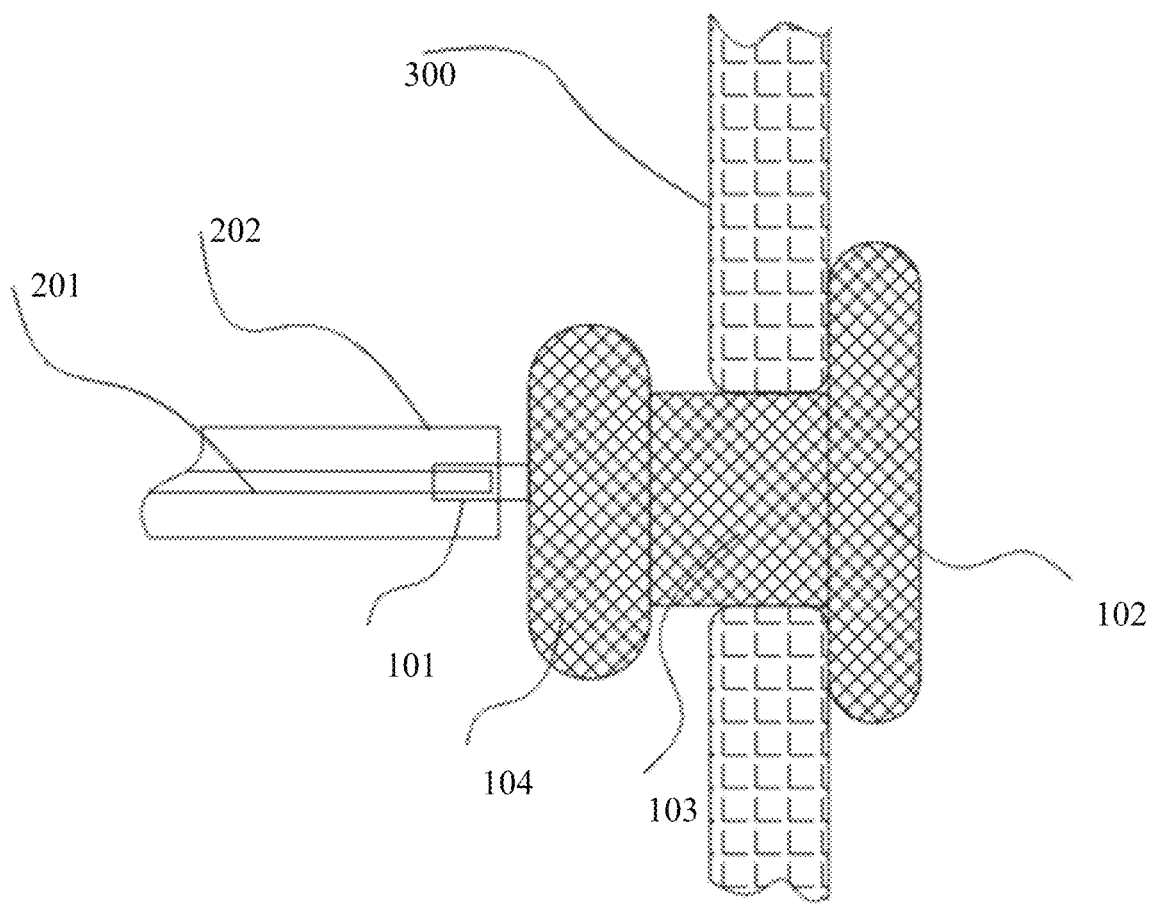
FIG. 6 demonstrates a schematic diagram of a release state of the right atrial wall fixing structure and the middle channel structure during the implementation of the first embodiment of the present invention.

Referring to FIG. 6, the pusher 201 is moved towards the right atrium while gradually releasing the middle channel structure 103. Finally, the right atrial wall fixing structure 104 adheres to the right atrial wall.

Figure 7:
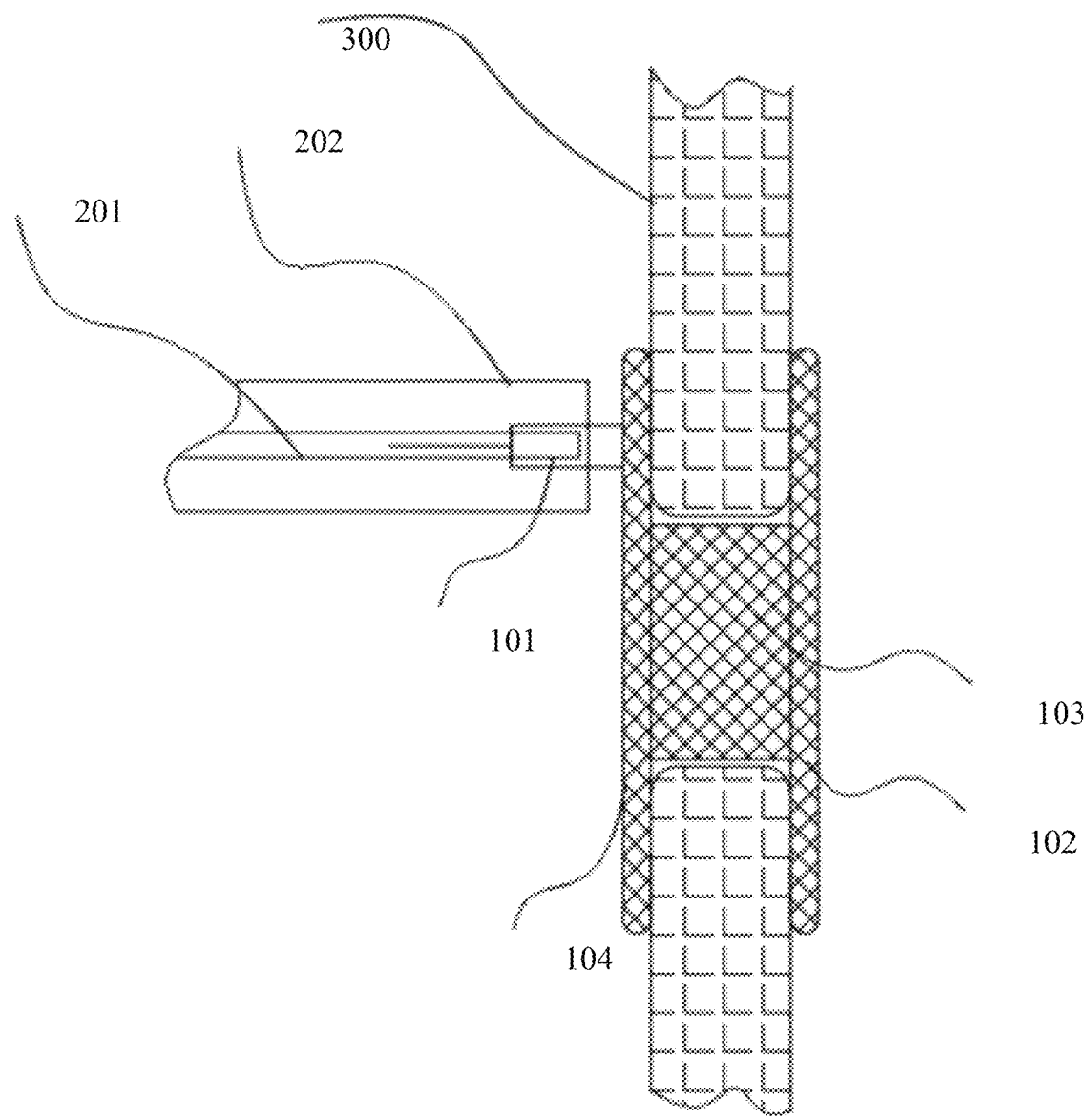
FIG. 7 represents a schematic diagram of a fully released state of the atrial shunt device during the implementation of the first embodiment of the present invention.

Referring to FIG. 7, after fully releasing the atrial shunt device 100, the fit between the device and the atrial wall 300 is examined. Subsequently, the connection between the pusher 201 and the delivery device connection structure 101 is disconnected by operation, and finally, the delivery device is withdrawn from the body.

In this embodiment, the delivery device connection structure 101, the left atrial wall fixing structure 102, the middle channel structure 103, and the right atrial wall fixing structure 104 connect the left atrium and right atrium, reducing atrial pressure, extending atrial lifespan, alleviating heart failure, and improving the success rate and convenience of the surgical procedure. The delivery device connection structure 101 possesses the functions of fixing the braided lines, connecting with the delivery device's pusher 201, and facilitating digital subtraction angiography (DSA).

In the actual research and development process, it was found that most atrial shunt devices 100 on the market are manually woven, and machine weaving is not feasible. The primary reason for this is that to ensure the device has sufficient support and generates adequate endothelialization between the device and the atrial wall 300, certain areas of the device need to be woven tightly when close to the left atrial wall, and other areas need to be woven loosely to maintain necessary resilience during device release. This means that the weaving needs to be balanced and appropriate.

Furthermore, current atrial shunt devices 100 on the market are mostly woven with metal wires such as nitinol. When certain areas of the device are woven tightly, the device becomes locally stiff. This stiffness can lead to reduced resilience after release, making it challenging to achieve proper device shape. Weavers need to strike a balance during the weaving process, avoiding being too loose, which results in inadequate support, and at the same time, avoiding being too tight, which leads to poor resilience. The difficulties in weaving are considerable.

Moreover, to overcome the challenges of weaving difficulty and poor resilience, current approaches often involve weaving the atrial shunt device 100 relatively loosely. However, when woven loosely, the device cannot form sufficient endothelialization with the atrial wall 300, leading to rejection reactions in the body. To achieve adequate endothelialization, many atrial shunt devices 100 are coated to obtain sufficient endothelialization. Nevertheless, coating is prone to excessive endothelialization, causing blockage of the opening in the atrial wall 300 and making the coating process complex.

Therefore, the current atrial shunt devices 100 face several challenging issues. The technical problems mentioned above are technical difficulties in the field of atrial shunt devices, and there is an urgent need in the market for an atrial shunt device 100 with balanced resilience and endothelialization and relatively simple manufacturing processes.

Figure 8:
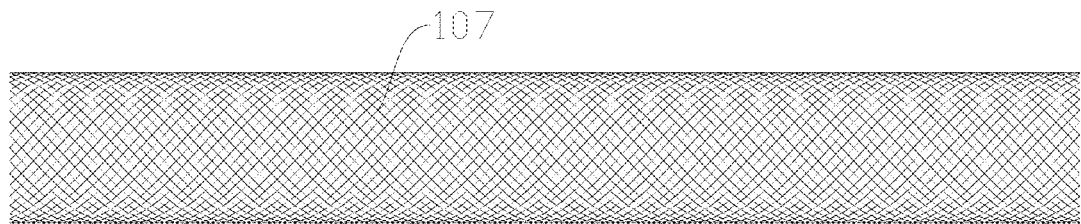
FIG. 8 provides a schematic structural diagram of the woven long cylinder in the first and second embodiments of the present invention.

To overcome the aforementioned issues, specifically, as illustrated in FIG. 8, the left atrial wall fixing structure 102, middle channel structure 103, and right atrial wall fixing structure 104 in this application are integrally woven and molded into a woven long cylinder 107, which is thermally shaped. This woven long cylinder 107 can be woven from nitinol wires or polymer materials, such as PLLA, PDO, and other biodegradable polymer materials.

Figure 9:
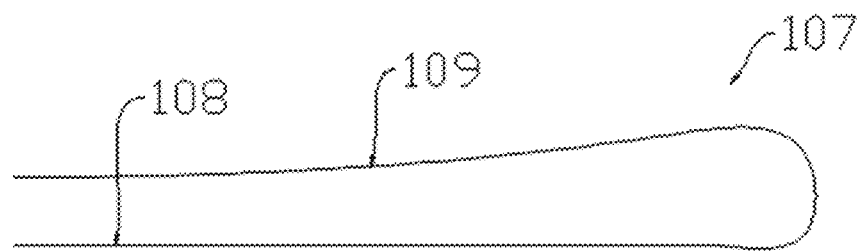
FIG. 9 illustrates a schematic structural diagram of the woven long cylinder in the first and second embodiments of the present invention when folded outward.
Figure 10:
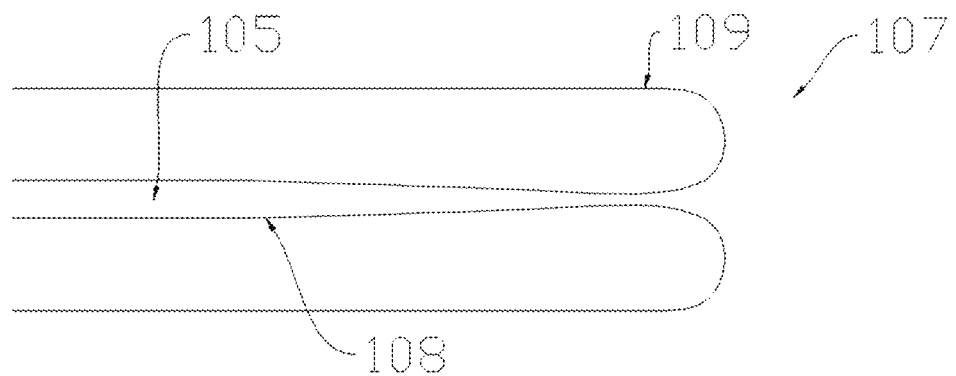
FIG. 10 shows a schematic structural diagram of the woven long cylinder in the first and second embodiments of the present invention when folded inward.

In detail, as shown in FIGS. 9 and 10, the woven long cylinder 107 can be folded outward or inward from the waist to form overlapping inner woven layer 108 and outer woven layer 109, with the inner woven layer 108 internally forming the connecting channel 105.

Figure 14:
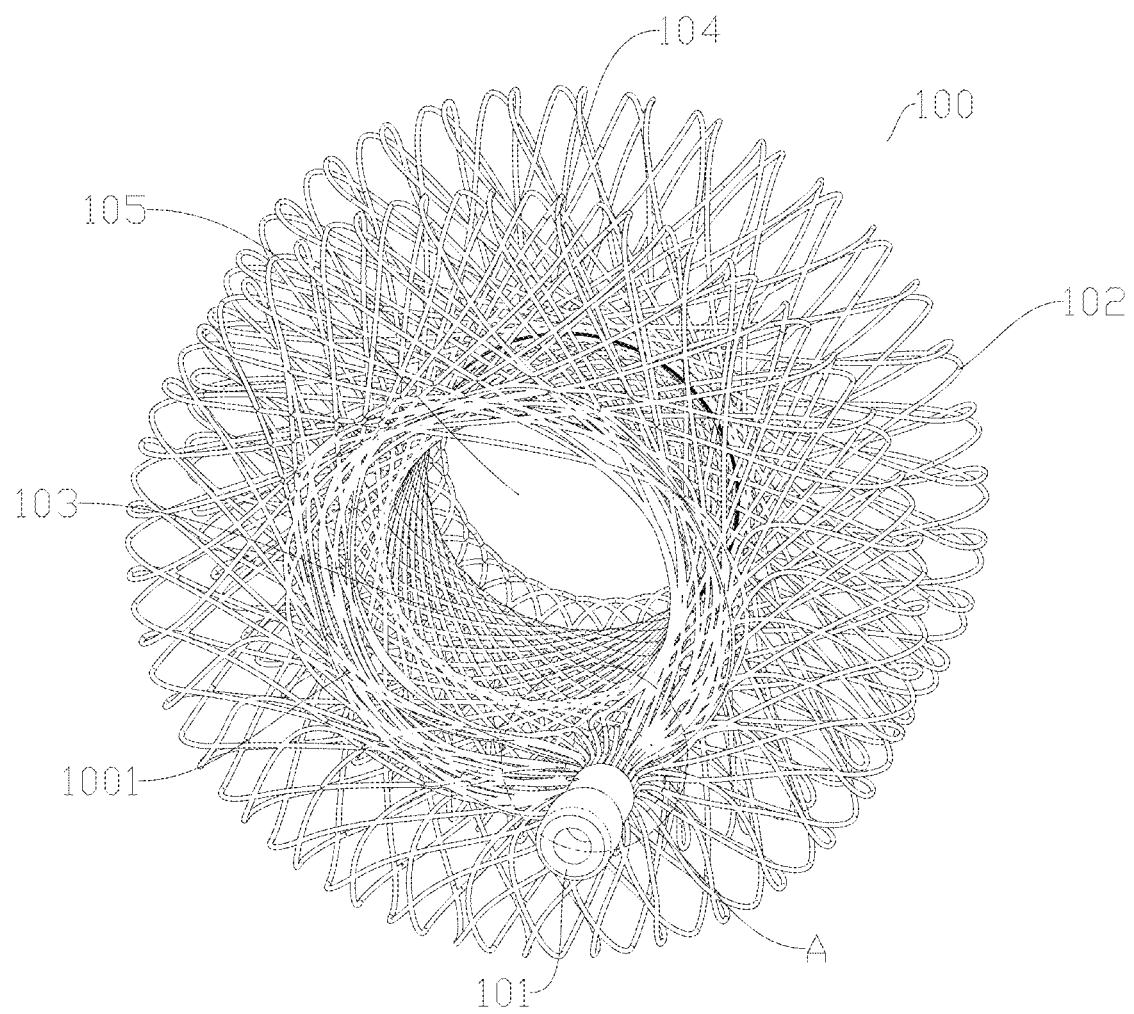
FIG. 14 is a structural diagram of an atrial shunt device in the first and second embodiments of the present invention.
Figure 15:
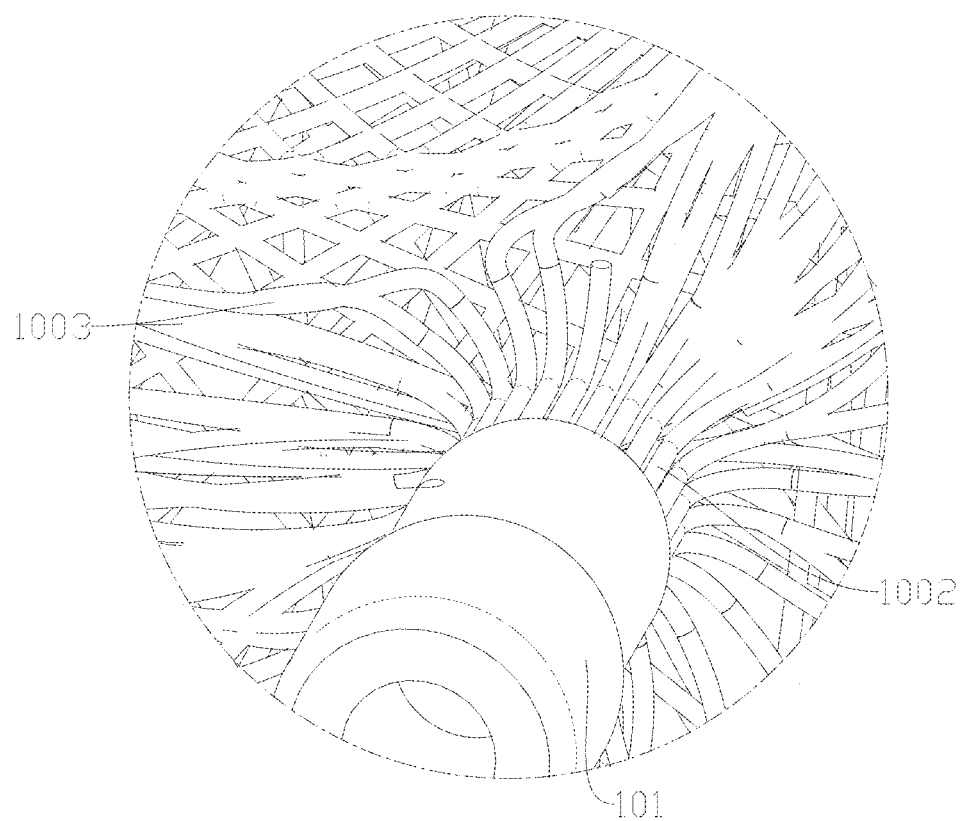
FIG. 15 provides an enlarged view of point A in FIG. 14.
Figure 16:
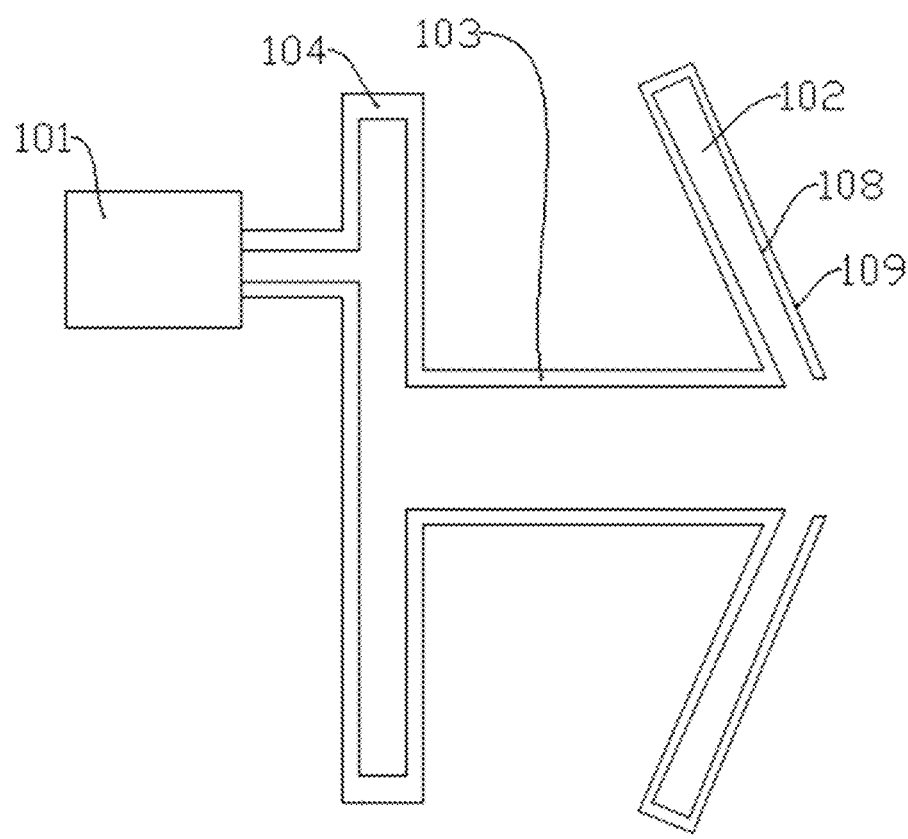
FIG. 16 is a simplified diagram of the cross-sectional view of an atrial shunt device in the first embodiment of the present invention.

Subsequently, as shown in FIGS. 11, 14, 15, and 16, after overlapping the proximal ends of the inner woven layer 108 and outer woven layer 109, they are radially folded and bound together to form a tail section 1002. A communication port 1001 in communication with the connecting channel 105 is formed at the proximal end of the atrial shunt device 100, and the delivery device connection structure 101 tightens the tail section 1002. Specifically, as shown in FIG. 15, one side of the proximal end 1003 of the atrial shunt device 100 is gathered together to form the tail section 1002, which can then be tightened using the delivery system fixing structure 100.

After thermal shaping the inner woven layer 108 and outer woven layer 109, they sequentially form the right atrial wall fixing structure 104, middle channel structure 103, and left atrial wall fixing structure 102 along the axis direction of the atrial shunt device 100.

Preferably, the woven long cylinder 107 is machine-woven; however, manual weaving is also feasible. In this application, as the left atrial wall fixing structure 102, middle channel structure 103, and right atrial wall fixing structure 104 are made from the integrally woven woven long cylinder 107, the weaving density at various locations on the woven long cylinder 107 can be identical. Therefore, in the actual production process, the woven long cylinder 107 can be machine-woven, greatly reducing the difficulty of weaving. However, manual weaving is also possible, as the weaving density can be uniform throughout, simplifying the weaving process.

Most importantly, as shown in FIGS. 1, 14, and 15, the atrial shunt device 100 in this embodiment ingeniously forms a communication port 1001 at the proximal end and leaves a tail section 1002 that can be fixed by the delivery system fixing structure. This approach not only forms a communication port 1001 at the proximal end of the atrial shunt device 100 but also provides a tail section 1002 that can be fixed by the delivery system fixing structure. It's truly a win-win. By using the exquisite manufacturing method of this application, the most ideal double-layer woven atrial shunt device 100 can be obtained with the simplest processing method.

Due to the simplicity of the processing method, the manufacturing cost of the atrial shunt device 100 will be reduced, benefiting numerous heart disease patients.

Furthermore, as the woven long cylinder 107 is folded to form the inner woven layer 108 and outer woven layer 109, the atrial shunt device 100 can not only obtain sufficient elasticity but also, with two layers of woven structure, enough wires contact the atrial wall 300, allowing for sufficient endothelialization.

Moreover, using the inner woven layer 108 and outer woven layer 109 as a double-layer woven structure, the weaving density of both layers does not need to be too high, facilitating subsequent thermal shaping. Excessive weaving density can make the woven layer stiff, hindering the thermal shaping process.

In summary, the atrial shunt device 100 in this application, using the form of inner woven layer 108 and outer woven layer 109, can be machine-woven and still maintain high resilience. The contact with the atrial wall 300 can achieve proper endothelialization. Additionally, based on the inventor's research, the optimum number of grids per inch for the woven long cylinder 107 in this application is 8 to 20. As the woven long cylinder 107 can be machine-woven, the amount of thread used for the entire atrial shunt device 100 can be precisely controlled (i.e., controlling the number of grids per inch within 8 to 20), ensuring that the atrial shunt device 100 achieves proper endothelialization with the atrial wall 300. This level of endothelialization can avoid rejection reactions and prevent excessive endothelialization, leading to blockage. Even if the endothelialization is slightly excessive, due to the multi-layer structure of the atrial shunt device 100, it has strong support and can support the opening, preventing blockage. Additionally, preferably, the distal ends of the inner woven layer 108 and outer woven layer 109 are overlapped and fixed together by a fixing element. Specifically, before thermal shaping the inner woven layer 108 and outer woven layer 109, the distal ends can be woven and overlapped with weaving wires, preventing misalignment of the distal ends of the inner woven layer 108 and outer woven layer 109.

It should be noted that the atrial shunt device 100 in this application is an internal type, meaning that once implanted in the body, it will not be removed from the body during its period of use.

Embodiment 2

The second embodiment of the present invention provides a manufacturing method for an atrial shunt device. The specific steps are as follows:

As shown in FIG. 8, use nitinol wires or polymer material weaving threads to integrally weave and form an woven long cylinder 107. Preferably, the number of grids per inch for the woven long cylinder 107 is 8 to 20, although in practice, it can exceed this range.

As shown in FIG. 9, fold the woven long cylinder 107 outward from the waist to form overlapping inner woven layer 108 and outer woven layer 109, with the inner woven layer 108 containing the connecting channel 105. In some embodiments, as shown in FIG. 10, the woven long cylinder 107 can also be folded inward from the waist to form overlapping inner woven layer 108 and outer woven layer 109.

Figure 11:
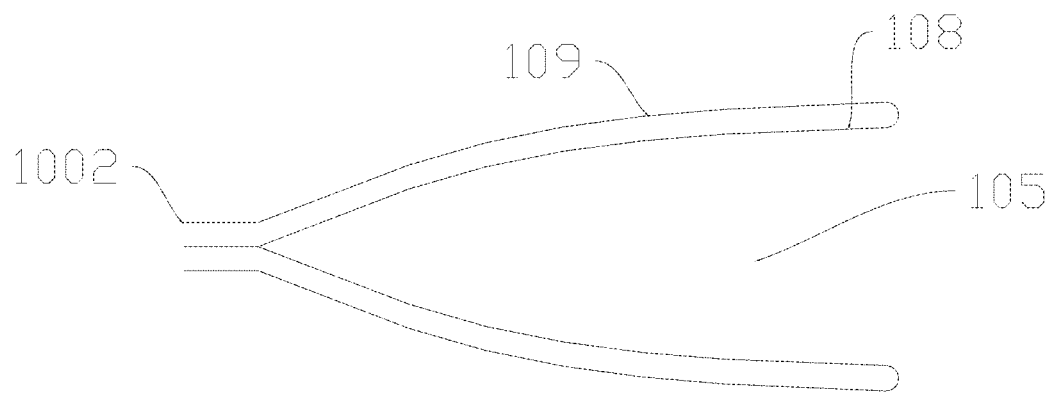
FIG. 11 presents a schematic structural diagram of the present invention in the first and second embodiments after folding the woven long cylinder and tightening the tail section.

As shown in FIG. 11, overlap the proximal ends of the folded inner woven layer 108 and outer woven layer 109, then radially fold and bind them together at one point to form tail section 1002. At this point, the proximal end of the atrial shunt device 100 forms a communication port 1001 in communication with the connecting channel 105. Tighten the above tail section 1002 to create a workpiece awaiting heat setting.

Thermally shape the workpiece awaiting heat setting, forming right atrial wall fixing structure 104, middle channel structure 103, and left atrial wall fixing structure 102 arranged sequentially from the proximal end to the distal end. The tail section 1002 is positioned on the right atrial wall fixing structure 104.

Use the delivery device connection structure 101 to fix the tail section 1002, and this connection structure 101 can connect to the delivery device used for transporting the atrial shunt device 100.

Since the left atrial wall fixing structure 102, middle channel structure 103, and right atrial wall fixing structure 104 are made from the integrally woven long cylinder 107, the weaving density at various locations on the woven long cylinder 107 can be identical. Therefore, in the actual production process, the woven long cylinder 107 can be machine-woven, significantly reducing the weaving difficulty. Manual weaving is also feasible, as the weaving density can be uniform throughout, reducing the weaving difficulty.

Moreover, due to the folding of the woven long cylinder 107 to form the inner woven layer 108 and outer woven layer 109, the atrial shunt device 100 can not only obtain sufficient elasticity but also, with two layers of woven structure, enough wires contact the atrial wall 300, allowing for sufficient endothelialization.

Furthermore, using the inner woven layer 108 and outer woven layer 109 as a double-layer woven structure, the weaving density of both layers does not need to be too high, facilitating subsequent thermal shaping. Excessive weaving density can make the woven layer stiff, hindering the thermal shaping process.

In conclusion, the atrial shunt device 100 in this application, using the form of inner woven layer 108 and outer woven layer 109, can be machine-woven and still maintain high resilience. The contact with the atrial wall 300 can achieve proper endothelialization.

Additionally, before thermally shaping the workpiece awaiting heat setting, reinforce the distal ends of the inner woven layer 108 and outer woven layer 109 using weaving wires, ensuring that the distal ends of the inner woven layer 108 and outer woven layer 109 are aligned. After reinforcement, the distal ends of the inner woven layer 108 and outer woven layer 109 can be fixed together, preventing misalignment.

Figure 12:
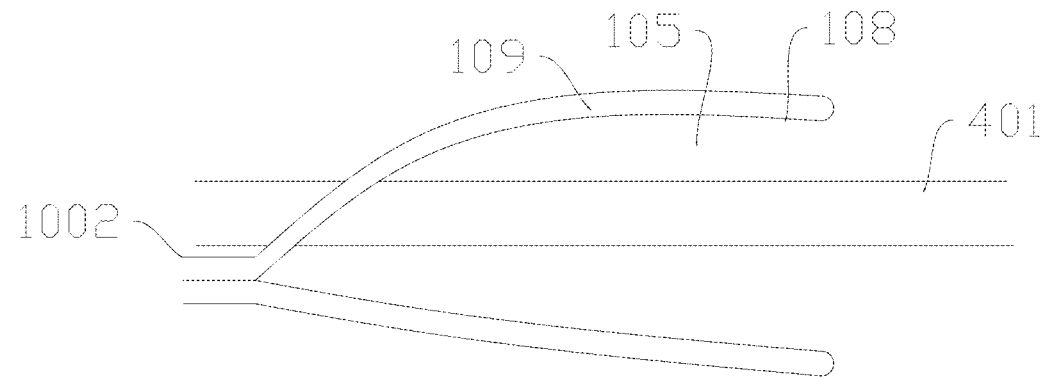
FIG. 12 exhibits a schematic structural diagram of after inserting the shaping rod into the connecting channel in the first and second embodiments of the present invention.

Moreover, specifically, in the step of thermally shaping the workpiece awaiting heat setting, the following steps are included:

As shown in FIG. 12, use a shaping rod 401 located in the communication port 1001 and the connecting channel 105. The shaping rod 401 can be inserted from the distal end of the atrial shunt device 100 into the connecting channel 105 and then exit from the communication port 1001. Of course, the shaping rod 401 can also be inserted from the proximal end's communication port 1001 into the connecting channel 105 and then exit from the distal end of the atrial shunt device 100.

Figure 13:
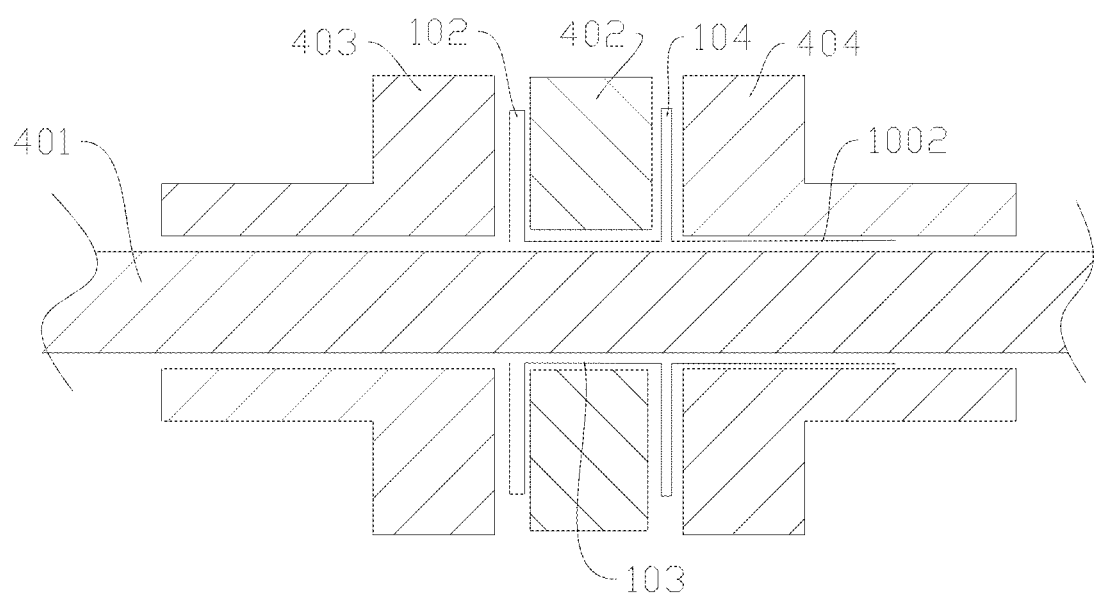
FIG. 13 displays a schematic structural diagram of mold components securing the atrial shunt device in the first and second embodiments of the present invention.

As shown in FIG. 13, use mold components to shape the workpiece awaiting heat setting into the shapes of the right atrial wall fixing structure 104, middle channel structure 103, and left atrial wall fixing structure 102, forming a to-heated piece. The to-heated piece includes the prototypical atrial shunt device 100 and the mold components.

Place the to-heated piece into an heating furnace for heating and shaping. After heating is completed, cool the atrial shunt device 100. Then, set the delivery device connection structure 101 on the tail section 1002, such as by pressing it onto the tail section 1002 or welding it in place. The atrial shunt device 100 is now complete.

Specifically, as shown in FIG. 13, the mold includes left mold 403, middle mold 402, and right mold 404. The middle mold 402 is placed over the shaping rod 401 and the workpiece awaiting heat setting. After fixing the middle mold 402, push the left side of the workpiece awaiting heat setting, causing the left side of the workpiece awaiting heat setting to bulge to form the left atrial wall fixing structure 102. Place the left mold 403 over the workpiece awaiting heat setting, clamping the left atrial wall fixing structure 102 between the middle mold 402 and the left mold 403, securing them together. This can be done with screws or by fixing the left atrial wall fixing structure 102 to the shaping rod 401. After fixing the left mold 403, push the right side of the workpiece awaiting heat setting, causing the right side of the workpiece awaiting heat setting to bulge to form the right atrial wall fixing structure 104. Place the right mold 404 over the workpiece awaiting heat setting, clamping the right atrial wall fixing structure 104 between the middle mold 402 and the right mold 404, securing them together. This can be done with screws or by fixing the right atrial wall fixing structure 104 to the shaping rod 401. It should be noted that the installation order of the left mold 403 and right mold 404 can be interchangeable; for example, the right mold 404 can be installed first, followed by the left mold 403. Once all molds are fixed, a to-heated piece is formed. Then, place the to-heated piece into the heating furnace for heating. After heating is completed, cool the atrial shunt device 100. After cooling is completed, remove the molds, obtaining the prototype of the atrial shunt device 100. Finally, fix the delivery device connection structure 101 on the tail section 1002, for example, by pressing it onto the tail section 1002, or welding it in place.

Due to the correspondence between the first implementation method and the present implementation method, the technical details mentioned in the second implementation method remain effective in the present implementation method. The technological effects achievable in the first implementation method can also be realized in the present implementation method. To avoid redundancy, details regarding this are not reiterated. Correspondingly, the technical details mentioned in the present implementation method can also be applied to the first implementation method.

Figure 17:
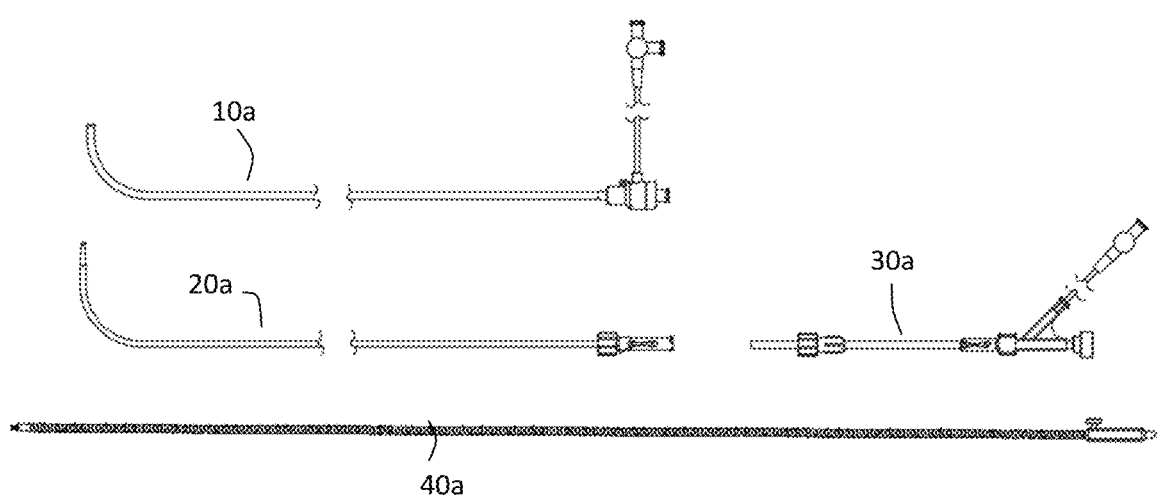
FIG. 17 illustrates a side view of an atrial shunt device delivery device in the second embodiment of the present invention.

The third embodiment of the present invention provides a shunting system for the atria, comprising the atrial shunt described in the previous embodiments and an atrial shunt delivery device, as shown in FIG. 17. The provided atrial shunt delivery device has a catheter sheath structure 10a, an expander structure 20a, a loading structure 30a, and a pushing structure 40a.

Since the shunting system for the atrium in this embodiment includes the atrial shunt from the first embodiment, and the left atrial wall fixing structure 102, intermediate channel structure 103, and right atrial wall fixing structure 104 in the atrial shunt of the first embodiment are woven into a woven long cylinder 107 in an integral manner, the weaving density at various locations on this woven long cylinder 107 can be completely the same. Therefore, in the actual production process, the woven long cylinder 107 can be woven by a machine, greatly reducing the weaving difficulty. Of course, manual weaving is also possible since the weaving density is the same at all locations. Furthermore, due to the folding of the woven long cylinder 107 into the inner woven layer 108 and outer woven layer 109, the atrial shunt 100 can not only obtain sufficient elasticity but also, with the two layers of woven mesh in the inner woven layer 108 and outer woven layer 109, have sufficient contact with the atrial wall 300, facilitating sufficient endothelialization.

Moreover, with the use of the inner woven layer 108 and outer woven layer 109 forming two layers of woven mesh, the weaving density of both the inner woven layer 108 and outer woven layer 109 does not need to be too dense, making it convenient for subsequent thermal setting of the atrial shunt 100. If the weaving is too dense, the weaving layer will become very hard, preventing subsequent thermal setting.

In summary, the atrial shunt 100 in this application, using the form of the inner woven layer 108 and outer woven layer 109, can be machine-woven and still maintain high resilience. It can also achieve proper endothelialization with the atrial wall 300.

Figure 18:
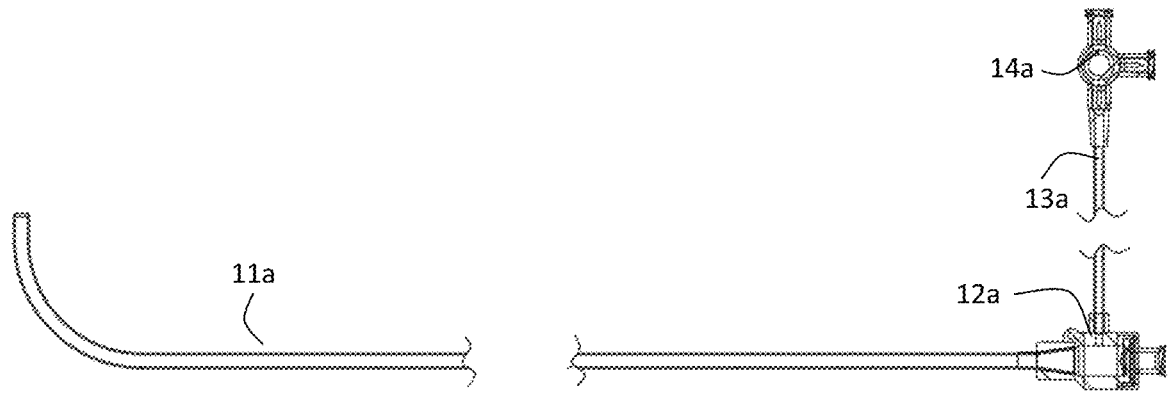
FIG. 18 depicts a side view of a catheter sheath structure 10a in the second embodiment of the present invention.
Figure 19:
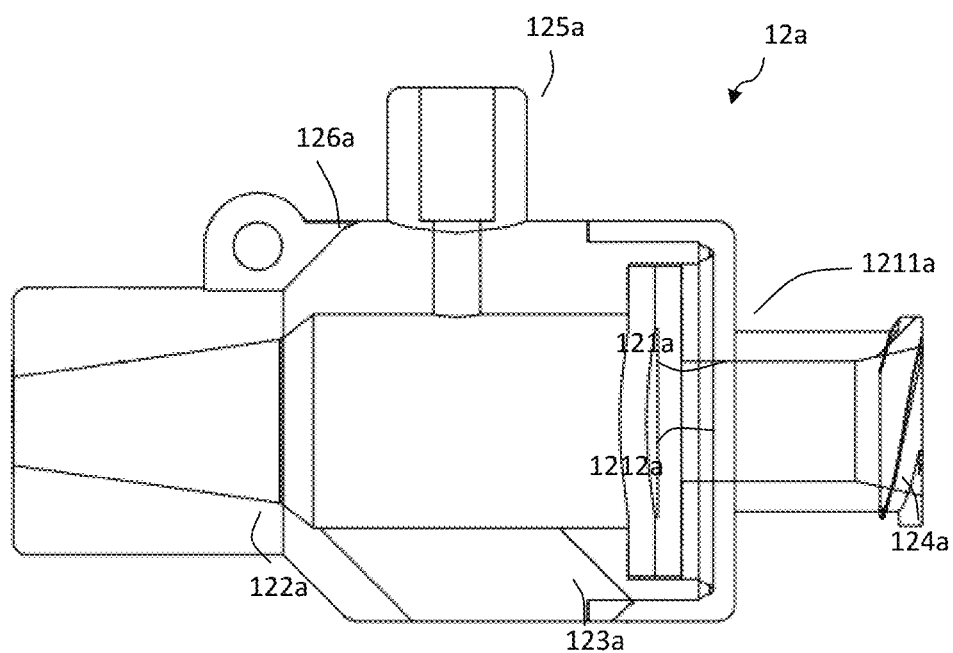
FIG. 19 presents a cross-sectional view of the catheter sheath handle 12a in the second embodiment of the present invention.

Additionally, specifically, as shown in FIGS. 18 to 19, the catheter sheath structure 10a has a pre-bent sheath tube 11a and a catheter sheath handle 12a. The middle and near segments of the pre-bent sheath tube 11a are straight but can also be curved, while the distal segment is curved. The catheter sheath handle 12a is connected to the proximal end of the pre-bent sheath tube 11a and has a hollow cylindrical body. Inside the cylindrical body, there is a sealing pad 121a with a needle hole, comprising a sealing flat pad 1211a and a sealing bent pad 1212a, with the latter tightly attached to the former. The sealing pad 121a has a needle hole in the middle, which, when no other components pass through, such as the expander structure 20a or the pushing structure 40a, is blocked by its own elasticity, preventing air leakage. The sealing bent pad 1212a is arc-shaped, ensuring that the expander structure 20a or pushing structure 30a can smoothly pass through the catheter sheath handle 12a. Also, due to the sealing nature of the sealing bent pad 1212a, it ensures that after the expander structure 20a has passed through, there will be no leakage from the catheter sheath handle 12a. The sealing flat pad 1211a ensures the sealing of the catheter sheath handle 12a when there are no instruments such as the expander structure 20a or pushing structure 30a inserted. The curvature radius of the sealing bent pad 1212a is 10-15 mm, preferably 12-13 mm. The protruding side of the sealing bent pad 1212a is located at the distal end, and the concave side is located at the proximal end. The thickness-to-diameter ratio of the sealing bent pad 1212a is 0.10-0.15:1, preferably 0.12-0.13:1; the same ratio for the sealing flat pad 1211a is also 0.10-0.15:1, preferably 0.12-0.13:1. The catheter sheath handle 12a, from the distal end to the proximal end, sequentially has a hollow sheath tube connection section 122a, a hollow middle section 123a, and a hollow loading connection section 124a, with the sealing bent pad 1212a and the sealing flat pad 1211a tightly attached to the proximal end of the middle section 123a. The inner cavity cross-section of the sheath tube connection section 122a is trapezoidal, and the loading connection section 124a's proximal end has a frustoconical entrance. The outer diameter of the sheath tube connection section 122a and the loading connection section 124a is smaller than the outer diameter of the middle section 123a. The inner diameter of the sheath tube connection section 122a and the loading connection section 124a is smaller than the inner diameter of the middle section 123a. The inner diameter of the sheath tube connection section 122a smoothly transitions to the inner diameter of the middle section 123a. The catheter sheath handle 12a has an exhaust port 125a, which communicates with the inner cavity of the middle section 123a. The catheter sheath handle 12a also has a fixation hole 126a, located on the external proximal end of the sheath tube connection section 122a. The catheter sheath structure 10a also has a TPU tube 13a and a three-way connector 14a, with one end of the TPU tube 13a connected to the exhaust port 125a of the catheter sheath handle 12a; the three-way connector 14a is connected to the other end of the TPU tube 13a.

Figure 20:
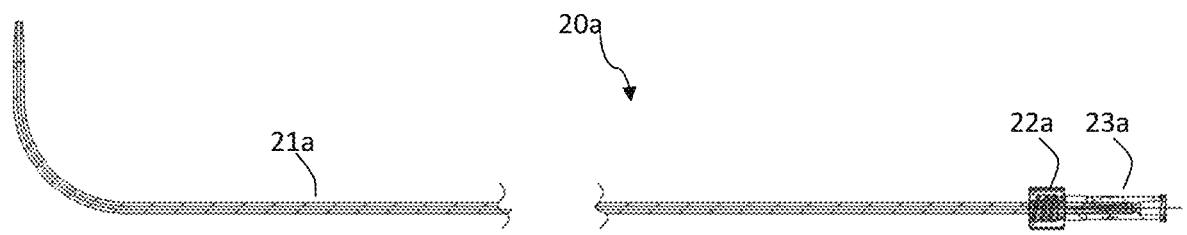
FIG. 20 provides a side view of an expander structure 20a in the second embodiment of the present invention.

As shown in FIG. 20, the expander structure 20a, when expanded, can sequentially pass through the catheter sheath handle 12a and the pre-bent sheath tube 11a of the catheter sheath structure 10a. The expander structure 20a has a pre-bent expansion tube 21a, an expansion ruler joint 22a, and an expansion handle 23a. The distal segment of the pre-bent expansion tube 21a is curved, and the middle and proximal segments are straight, but can also be curved; during expansion, it can sequentially pass through the catheter sheath handle 12a and the pre-bent sheath tube 11a of the catheter sheath structure 10a. The expansion ruler joint 22a is connected to the proximal end of the pre-bent expansion tube 21a. The expansion handle 23a is connected to the proximal end of the expansion ruler joint 22a.

Figure 21:
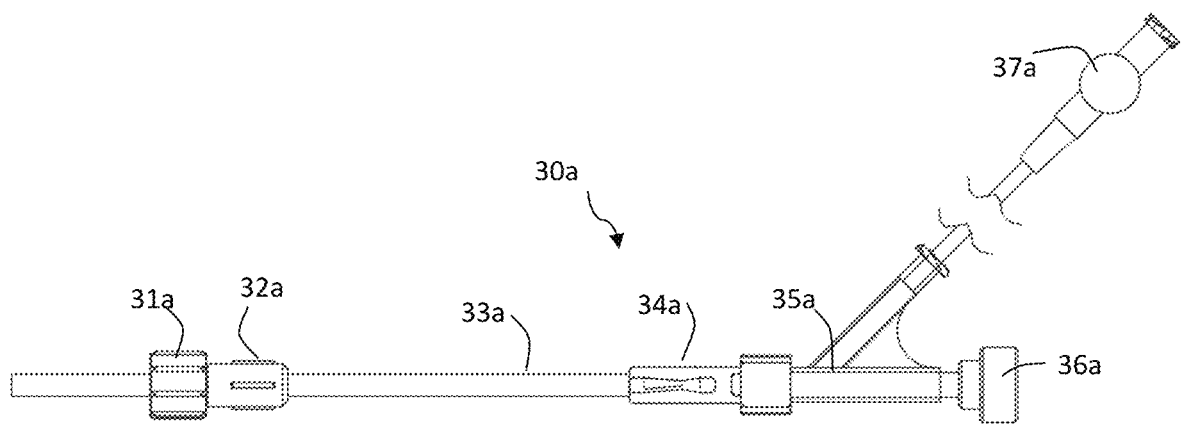
FIG. 21 displays a side view of a loading structure 30a in the second embodiment of the present invention.
Figure 22:
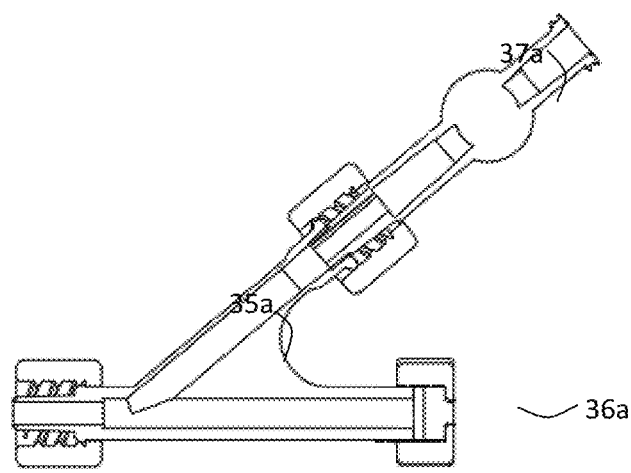
FIG. 22 illustrates a side view of a Y-shaped hemostatic valve 35a in the loading structure 30a of the second embodiment of the present invention.

As shown in FIGS. 21-22, the loading structure 30a, when loading the atrial shunt 100, can communicate with the catheter sheath handle 12a of the catheter sheath structure 10a. The loading structure 30a has a loading ruler joint 31a, which, when loading the atrial shunt, can communicate with the catheter sheath handle 12a of the catheter sheath structure 10a; a distal handle 32a is connected to the proximal end of the loading ruler joint 31a; a loading tube 33a is connected to the distal end of the loading ruler joint 31a; a proximal handle 34a is connected to the proximal end of the loading tube 33a; one end of a Y-shaped hemostatic valve 35a is connected to the proximal end of the proximal handle 34a; an adjustable hemostatic valve 36a is connected to the other end of the Y-shaped hemostatic valve 35a; and a two-way connector 37a is connected to the third end of the Y-shaped hemostatic valve 35a.

Figure 23:
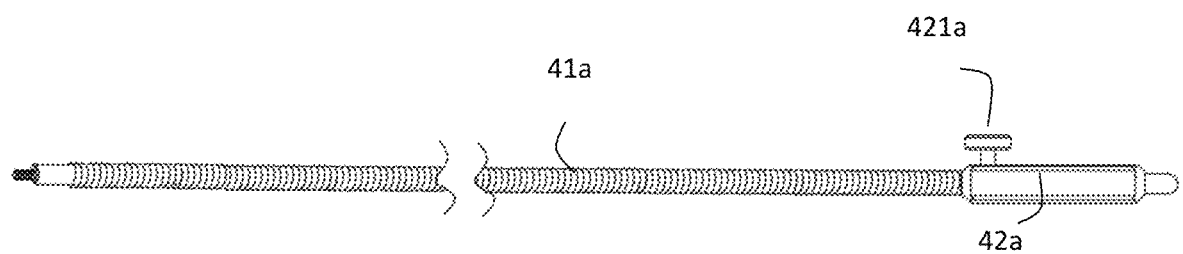
FIG. 23 shows a side view of a pushing structure 40a in the second embodiment of the present invention.

As shown in FIG. 23, the pushing structure 40a, when pushing the atrial shunt 100, can sequentially pass through the Y-shaped hemostatic valve 35a, the proximal handle 34a, the loading tube 33a, the distal handle 32a, and the loading ruler joint 31a of the loading structure 30a, as well as the catheter sheath handle 12a and the pre-bent sheath tube 11a of the catheter sheath structure 10a. The pushing structure 40a has a push rod 41a, which, when pushing the atrial shunt 100, can sequentially pass through the Y-shaped hemostatic valve 35a, the proximal handle 34a, the loading tube 33a, the distal handle 32a, and the loading ruler joint 31a of the loading structure 30a, as well as the catheter sheath handle 12a and the pre-bent sheath tube 11a of the catheter sheath structure 10a. A detachment handle 42a is connected to the proximal end of the push rod 41a via a fixing screw 421a.

Figure 24:
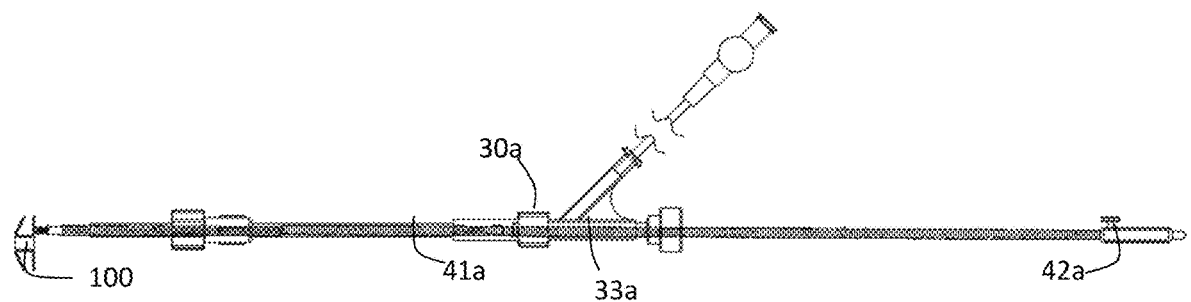
FIG. 24 shows a process reference diagram for use of an atrial shunt device delivery device in the second embodiment of the present invention.

The atrial shunt delivery device in this embodiment can be used after the "transseptal technique" (i.e., inserting the pre-bent sheath tube 11a of the catheter sheath structure 10a into the right femoral vein, going upwards along the inferior vena cava into the right atrium, then puncturing the septum and inserting the pre-bent sheath tube 11a of the catheter sheath structure 10a into the left atrium). The expander structure 20a is loaded into the catheter sheath structure 10a, and the pre-bent sheath tube 11a enters the body along the guide wire. As shown in FIG. 24, the atrial shunt 100 is loaded into the loading structure 30a's loading tube 33a using the loading structure 30a and the pushing structure 40a, starting from the proximal end of the catheter sheath handle 12a, and implanting the atrial shunt 100 into the interatrial septum.

Figure 25:
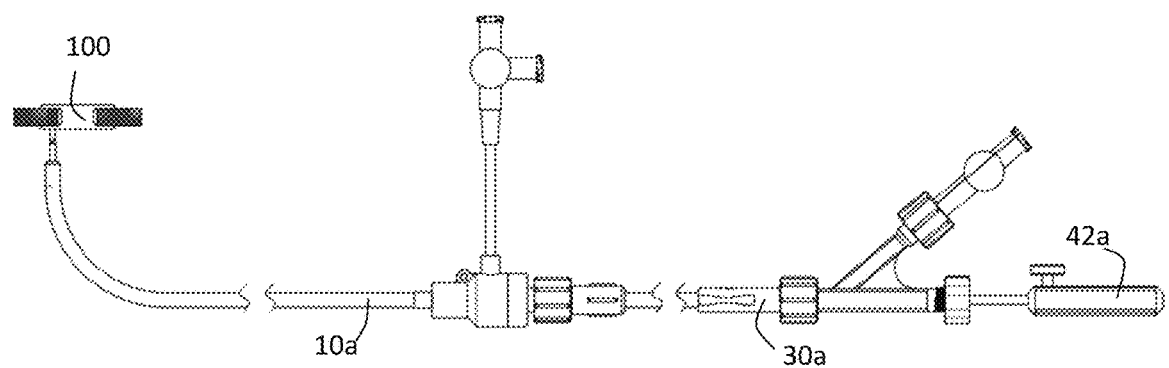
FIG. 25 shows another process reference diagram for use of aan atrial shunt device delivery device in the second embodiment of the present invention.

As shown in FIG. 25, after completely releasing the atrial shunt 100, the fit between the atrial shunt 100 and the atrial wall is checked. Subsequently, the detachment handle 42a of the pushing structure 40a is rotated to release the atrial shunt 100, and finally, the atrial shunt delivery device is withdrawn from the body.

Since the first implementation method and the second embodiment correspond to the present implementation method, the present implementation method can be mutually coordinated with the first implementation method and the second embodiment. The technical details mentioned in the first implementation method remain effective in the present implementation method, and the technological effects achievable in the first implementation method can also be realized in the present implementation method. To avoid repetition, details regarding this are not reiterated. It should be noted that the terms "distal," "proximal," "distal segment," and "proximal segment" used as directional terms in this invention are conventional terms in the field of interventional medical devices. "Distal" and "distal segment" refer to one end or segment away from the operator during surgery, while "proximal" and "proximal segment" refer to one end or segment close to the operator. Axial refers to the direction parallel to the line connecting the distal and proximal centers of the interventional medical device; radial refers to the direction perpendicular to the axial direction.

The above illustrates and describes the basic principles, main features, and advantages of the present invention. Those skilled in the art should understand that the present invention is not limited to the above embodiments. The embodiments and descriptions provided are merely illustrative of the principles of the present invention. Various changes and improvements may be made without departing from the spirit and scope of the present invention. The scope of protection of the present invention is defined by the appended claims and their equivalents.

What is claimed is:

1. An atrial shunt device comprising a middle channel structure with a left atrial wall fixing structure and a right atrial wall fixing structure on both sides respectively;
    wherein the left atrial wall fixing structure is a woven mesh structure woven from one or more wires using a braiding process, and the woven mesh structure includes at least two layers of woven layers; the left atrial wall fixing structure, the middle channel structure, and the right atrial wall fixing structure are formed through heat-setting molding from an integrally braided woven long cylinder;
    the atrial shunt device further includes a delivery device connection structure for connection to a delivery device; the woven long cylinder is folded outward or inward from a middle waist position to form an inner woven layer and an outer woven layer overlapping with the inner woven layer, with the inner woven layer forming a connecting channel;
    after proximal ends of the inner woven layer and the outer woven layer overlap, they are radially bent and bound together to form a tail section, and the delivery device connection structure tightens the tail section, and a communication port is formed at the proximal end of the atrial shunt device, communicating with the connecting channel;
    the inner woven layer and the outer woven layer are heat-set to form the right atrial wall fixing structure, the middle channel structure, and the left atrial wall fixing structure sequentially along the axis direction of the atrial shunt device.

2. The atrial shunt device of claim 1, wherein the number of grids per inch of the woven long cylinder is 8 to 20.

3. The atrial shunt device of claim 1, wherein distal ends of the inner woven layer and the outer woven layer are overlapped and fixed by a fixing member, bringing the distal ends of the inner woven layer and the outer woven layer into close contact.

4. The atrial shunt device of claim 1, wherein the distal ends of the inner woven layer and the outer woven layer are overlapped and braided together with one or more wires.

5. The atrial shunt device of claim 1, wherein the one or more wires are selected from nickel-titanium wire, platinum-iridium wire, or a combination thereof;
the diameters of the one or more wires are 0.08 mm to 0.15 mm.

6. The atrial shunt device of claim 1, wherein the woven mesh structure comprises of 2 to 4 layers of woven layers, and a single layer of the woven layers is woven from the wire using a braiding process.

7. The atrial shunt device according to claim 6, wherein the middle channel structure and the right atrial wall fixing structure use the same wire and the same number of woven layers as the left atrial wall fixing structure;
the left atrial wall fixing structure, the middle channel structure, and the right atrial wall fixing structure are integrally woven and then heat-set molded.

8. The atrial shunt device of claim 1, further comprising a delivery device connection structure, with its distal end connected to the right atrial wall fixing structure and its proximal end connectable to a delivery device.

9. The atrial shunt device of claim 8, wherein an outer peripheral surface of the delivery device connection structure is provided with a ring of grooves to secure an external ring sleeve for the retrieval of the atrial shunt device.

10. The atrial shunt device of claim 8, wherein the proximal end of the delivery device connection structure has internal threads or external threads for threaded connection with the delivery device;
the material of the delivery device connection structure is selected from stainless steel, nickel-titanium alloy, platinum-iridium alloy, or a combination thereof.

11. The atrial shunt device of claim 1, further comprising a connecting channel passing through a middle of the left atrial wall fixing structure, the middle channel structure, and the right atrial wall fixing structure;
the diameters of the left atrial wall fixing structure and the right atrial wall fixing structure are both 15 mm to 25 mm;
the middle channel structure is a hollow cylindrical structure with openings on both left and right sides, and a middle of the hollow cylindrical structure serves as the connecting channel, a proximal outer peripheral surface of the middle channel structure is connected to the right atrial wall fixing structure, and a distal outer peripheral surface is connected to the left atrial wall fixing structure;
the inner diameter of the hollow cylindrical structure is 3 mm to 15 mm, and the length is 5 mm to 15 mm.

12. A manufacturing method for an atrial shunt device, comprising the following steps:
integrally weaving to form a woven long cylinder;
folding the woven long cylinder outward or inward from a middle waist to form overlapping inner woven layers and outer woven layers, with the inner woven layer forming a connecting channel;
after proximal ends of the inner woven layers and the outer woven layers overlap, they are bent radially and bound together to form a tail section, and a communication port is formed at a proximal end of the atrial shunt device, communicating with the connecting channel;
tightening the tail section to form a workpiece awaiting heat setting;
heat-setting the workpiece awaiting heat setting to form a right atrial wall fixing structure, a middle channel structure, and a left atrial wall fixing structure sequentially arranged from proximal to distal, with the tail section located on the right atrial wall fixing structure;
fixing the tail section with a delivery device connection structure for connection to a delivery device.

13. The manufacturing method of the atrial shunt device according to claim 12, wherein before heat-setting the workpiece awaiting heat setting, one or more wires are used to reinforce a distal end of the inner woven layer and a distal end of the outer woven layer, bringing the distal ends of the inner woven layer and the outer woven layer into close contact.

14. The manufacturing method of the atrial shunt device according to claim 12, wherein the steps of heat-setting the workpiece awaiting heat setting comprising:
(a) locating a shaping rod in the communication port and the connecting channel;
(b) shaping the workpiece awaiting heat setting into the shapes of the right atrial wall fixing structure, middle channel structure, and left atrial wall fixing structure with mold components to form a to-heat piece;
(c) placing the to-heat piece into a heating furnace for heat treatment;
(d) cooling the completed heated atrial shunt device.

15. The manufacturing method of the atrial shunt device according to claim 14, wherein step (b) comprising the following specific steps:
setting a middle mold over the shaping rod and the workpiece awaiting heat setting;
s1: pushing a right side of the workpiece awaiting heat setting to form the right atrial wall fixing structure, setting a right mold over the workpiece awaiting heat setting, clamping the right atrial wall fixing structure between the middle mold and the right mold, fixing the right mold;
s2: pushing a left side of the workpiece awaiting heat setting to form the left atrial wall fixing structure, setting a left mold over the workpiece awaiting heat setting, clamping the left atrial wall fixing structure between the middle mold and the left mold, fixing the left mold;
steps s1 and s2 can be interchanged;
after completing steps s1 and s2, the to-heat piece is formed.

16. A shunt system for atria, comprising the atrial shunt device of claim 1 and further includes an atrial shunt device delivery device; wherein the atrial shunt device delivery device has a catheter sheath structure, and the catheter sheath structure has:
a pre-bent sheath tube with a bent shape at a distal end; and
a catheter sheath handle, connected to a proximal end of the pre-bent sheath tube, the catheter sheath handle having a hollow cylindrical main body, and the interior of the main body having sealing pads with a needle hole, wherein the sealing pads comprise a sealing flat pad and a sealing bent pad, the sealing bent pad tightly abuts against the sealing flat pad.

17. The shunt system for atria according to claim 16, wherein curvature radius of the sealing bent pad is 10 to 15 mm, and a raised side of the sealing bent pad is located at the distal end, and a concave side is located at the proximal end.

* * * * *